United States Patent [19]
Brink et al.

[11] Patent Number: 4,901,738
[45] Date of Patent: Feb. 20, 1990

[54] LASER SHIELD

[75] Inventors: Robert H. Brink; James H. C. Harper; Steven T. Link, all of St. Paul, Minn.

[73] Assignee: Minnesota Mining and Manufacturing Company, St. Paul, Minn.

[21] Appl. No.: 285,324

[22] Filed: Dec. 13, 1988

Related U.S. Application Data

[63] Continuation of Ser. No. 33,004, Mar. 31, 1987, abandoned, which is a continuation-in-part of Ser. No. 865,518, May 21, 1986, abandoned.

[51] Int. Cl.$^4$ .................. A61F 13/00; A61B 17/36; B32B 31/00; B60R 13/00
[52] U.S. Cl. .................................. 128/849; 128/858; 156/272.8; 428/31; 606/2
[58] Field of Search ............... 128/849, 846, 850, 851, 128/853, 854, 855, 857, 858, 156, 303.1; 428/442, 31, 408; 156/272.8, 64

[56] References Cited

U.S. PATENT DOCUMENTS

| | | | |
|---|---|---|---|
| 1,611,031 | 12/1926 | Henderson | 428/236 |
| 3,009,077 | 11/1961 | Hansen | 128/849 |
| 3,367,329 | 2/1968 | Dibelius | 128/156 |
| 3,455,302 | 7/1969 | Liloia et al. | 128/132 R |
| 3,482,567 | 12/1969 | Franklin | 128/849 |
| 3,763,858 | 10/1973 | Buese | 128/156 |
| 4,009,453 | 2/1977 | Mahlein | 331/94.5 C |
| 4,023,119 | 5/1977 | Danielewicz, Jr. | 331/94.5 C |
| 4,024,862 | 5/1977 | Collins | 128/132 D |
| 4,139,409 | 2/1979 | Macken et al. | 156/634 |
| 4,204,532 | 5/1980 | Lind et al. | 128/132 D |
| 4,375,811 | 3/1983 | Sabbota et al. | 604/97 |
| 4,450,845 | 5/1984 | Engel | 128/743 |
| 4,519,798 | 5/1985 | Dinius | 604/358 |
| 4,520,053 | 5/1985 | Marentic | 428/31 |
| 4,520,814 | 6/1985 | Weeks | 128/303.1 |
| 4,558,093 | 12/1985 | Hatzenbuhler et al. | 524/837 |
| 4,597,382 | 7/1986 | Perez, Jr. | 128/17 |
| 4,601,286 | 7/1986 | Kaufman | 128/132 D |
| 4,604,998 | 8/1986 | Bellina | 128/132 D |
| 4,611,588 | 9/1986 | Laptewicz, Jr. et al. | 128/132 R |
| 4,616,641 | 10/1986 | Teeple | 128/132 R |
| 4,622,174 | 11/1986 | McKoy et al. | 252/582 |
| 4,635,625 | 1/1987 | Teeple | 128/163 |
| 4,715,366 | 12/1987 | Teeple | 128/849 |
| 4,743,499 | 5/1988 | Volke | 128/156 X |
| 4,765,323 | 8/1988 | Poettgen | 128/156 X |

FOREIGN PATENT DOCUMENTS 2207387 2/1972 Fed. Rep. of Germany ... 128/303.1
2821264 11/1978 Fed. Rep. of Germany ... 128/303.1

OTHER PUBLICATIONS

Article entitled "Laser Shields Prevent Accidental Exposure", Clinical Laser Monthly, vol. 43, No. 12 (Dec. 1985), p. 142.
Advertisement from Lasersafe TM, Inc., Pittsburgh, Pa. for Lasersafe TM Sterile Field Drape.
Article from Laser Consultants, Inc. entitled Laser Training Manual, Copyright 1984, pp. 75 and 76.
Article by John W. Brophy, M.D., entitled "Argon Laser Selectively Vaporizes Papillomas, Polyps in Vocal Cord," Clinical Laser Monthly, vol. 3, No. 11 (Nov. 1985), p. 3S.
Letter dated Sep. 20, 1985 to Dr. Robert H. Brink, PhD (Applicant) from P. S. Pomeroy, Senior Product Manager, Surgical Products, Kimberly-Clark.

Primary Examiner—Robert A. Hafer
Assistant Examiner—D. N. Muir
Attorney, Agent, or Firm—Donald M. Sell; Walter N. Kirn; Jennie G. Boeder

[57] ABSTRACT

A laser shield is constructed from a non-linting fabric sheet and a metal layer. The shield can be used as a laser-resistant surgical drape during laser surgery to protect the patient from aberrant laser strikes. The laser shield resists penetration by commonly-used surgical lasers, is non-reflective and flame resistant, and provides ready detection of any laser beam which strikes it.

26 Claims, 1 Drawing Sheet

LASER SHIELD

This is continuation of application Ser. No. 033,004 filed Mar. 31, 1987, now abandoned, which is a continuation-in-part of application Ser. No. 865,518 filed May 21, 1986; now abandoned.

BACKGROUND OF THE INVENTION

1. Field of the Invention

This invention relates to a laser shield which has particular utility in surgical applications.

2. Description of the Prior Art

High-powered lasers are now being widely used in medical therapy and surgical techniques to remove and/or repair tissues. A need exists for a laser-resistant surgical drape to protect the patient and prevent burning of tissues and other objects in the surgical field. Solid metallic shields often used to absorb or reflect laser radiation are not adaptable as a surgical drape since they are not flexible and would reflect too much of the laser radiation (a potential hazard). Wet towels are sometimes used in surgical applications for laser protection but they offer only about 0.5 seconds of protection or less (per layer) and are limited to protection from $CO_2$ lasers. Furthermore, the use of wet materials requires the operating room staff to moisten the material and monitor the material for dryness throughout the operating procedure.

Surgical packs and drapes commercially available as "Spunguard®) Surgical Packs and Gowns" from Kimberly-Clark Corporation, Roswell, Ga., are made entirely of polypropylene fibers and do not ignite when exposed to a defocused laser beam. However, these drapes do not prevent penetration by the laser beam and potential burning of patient tissue beneath the drape.

Lasersafe, Inc. Pittsburgh, Pa., has developed a series of aluminum shields for eyes and equipment. These shields are constructed with cotton gauze on the interior side and aluminum on the exterior. These products strongly reflect the laser beam creating the possibility that it may strike the patient or operating room staff. Furthermore, the gauze material used would not be suitable in a surgical drape since it is a linting material which can both cause granuloma and carry bacteria.

Aluminum tape is recognized as good protection for endotracheal tubes during otolaryngeal laser surgery. There is concern, however, that reflection of radiation from the metal may spuriously strike the patient or other operating room personnel.

U.S. Pat. No. 4,558,093 discloses a laser shield for use in surgical applications. The shield consists of densely-packed bubbles encapsulated in a matrix of silicone. The bubbles can be water bubbles and/or glass bubbles which may be filled with gas. The shields are said to be useful to terminate $CO_2$ laser radiation.

SUMMARY OF THE INVENTION

A laser shield useful in the field of operation during laser surgery comprises at least one opaque flexible nonwoven, knit or woven fabric sheet which has at least one major surface juxtaposed with a metal layer. The fabric sheet is relatively lint free, having 40 or less pieces of lint/cm$^2$. Additionally, if the fabric sheet is made from nonwoven fibers, preferably at least 10 percent of the fibers have lengths greater than about 0.6 cm. The metal layer is thick enough to resist puncture by a $CO_2$ laser beam using 5 watts of power and having a 2.0 mm diameter focus for at least about 0.2 second. Preferably, the metal layer is thick enough to resist puncture by a $CO_2$ laser beam using 20 watts of power and having a 0.4 mm diameter focus for at least about one second. Further the metal layer and the fabric sheet are thin enough to provide the shield with a rigidity of less than about 60,000 kg.mm.

The laser shields of this invention resist puncture by most lasers, powers and beam widths commonly used in laser surgery, including $CO_2$, Argon and Neodymium YAG lasers for periods of time generally in excess of two seconds.

The laser shields have particular applicability as laser-resistant surgical drapes. In such applications the fabric sheet side of the drape is towards the laser. The laser strikes the drape, penetrating the top fabric sheet and revealing the metal layer below. Thus, the drapes of this invention offer immediate detection of any aberrant laser strikes. As compared to metal shields alone, the laser-resistant drapes have better drapeability, more strength, more tear resistance, more resistance to wrinkling, result in no reflective glare and provide immediate detection of aberrant laser strikes. As compared to conventional cloth surgical drapes, the laser-resistant drapes of this invention are laser puncture resistant and are less flammable.

DETAILED DESCRIPTION OF THE INVENTION

Figure 1:
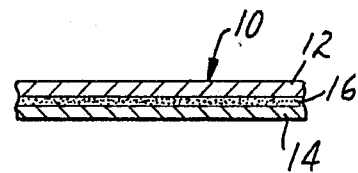
FIG. 1 is a cross-sectional view of one embodiment of this invention.

Referring to FIG. 1 of the drawings, the laser shield 10, in its simplest form, comprises a sheet 12 of fabric with a metal layer 14 juxtaposed with one major surface thereof. Attachment of metal layer 14 to fabric sheet 12 may be accomplished by adhesive layer 16, or by other suitable means such as heat laminating or mechanical fastening means.

For surgical applications as a surgical drape or gown, the fabric sheet 12 can be made from any flexible woven, knit or nonwoven opaque fabric materials suitable for use in surgical draps or gowns. Fabric materials for such surgical applications should be relatively lint free. The lint-free property is needed since lint can both carry bacteria and cause granuloma. The lint-free property is determined, by a test developed by the Dexter Corporation, Windsor Locks, Conn. The test involves placing a pressure-sensitive adhesive comprising an isooctylacrylate acrylic acid copolymer, commercially available as "Scotch ® Tape #681" from 3M Co., St. Paul, Minn., on the fabric sheet; pulling the tape from the fabric; and counting the number of fibers under a microscope. Preferably, the number of fibers should be 40 pieces/cm$^2$ or less, and more preferably 10 pieces/cm$^2$ or less, in order for the fabric to be considered lint free.

In more detail the lint test is conducted as follows. Two 10.16 cm×15.24 cm (4 in.×6 in.) pieces of polyethylene film are cut per side of fabric to be tested. Five holes (2 cm in diameter) are die cut in the film. A piece of "Scotch ® Tape #681," 5.08 cm (2 in.) in length, is placed at a 45° angle to the machine direction of the fabric to be tested. The tape is laminated to the fabric using a 363.2 g (0.8 lb) roller, 8 times, 2.54 cm (1 in.) per second, with no additional pressure. A piece of "Scotch" Tape #681," 15.24 cm (6 in.) in length, is placed over the holes on each piece of polyethylene film. This is done on a clean, lint-free surface. The tape is removed from the fabric sheet by hand at a 15° angle. This tape is placed on one piece of the film, over the holes, with the sticky side of the linty tape in contact with the sticky side of the clean tape. This sample and the film without the linty tape are compared under a microscope at 20×. This is done on top of a smooth lint-free black surface. The pices of lint in one circle of the linty tape sample are counted, using the criteria that the particle must have at least a 10:1 length to width ratio to be lint. That number is divided by 0.79 to arrive at pieces of lint/cm$^2$.

Preferred nonwoven fabric sheets are made from wood pulp; fibers of a thermoplastic polymeric material, including melt-blown polymer fibers, such as melt-blown polypropylene fibers, and synthetic polymer fibers, such as polypropylene, polyester, polyethylene, polyolefin, polyamide and nylon fibers; cellulosic nonwoven fibers such as nonwoven rayon; and combinations of these materials. The term "thermoplastic" is used herein to refer to materials which are solid at room temperature (22°-30° C.), but which soften or melt when heated to temperatures above room temperature. Thermoplastic materials are extrudable at temperatures in excess of 50° C. Preferred thermoplastic materials soften or melt at temperatures above about 50° C. and below about 1,000° C., in order that the material will not melt during transportation but be melted by commonly-used surgical lasers. More preferred thermoplastic materials soften or melt at temperatures between 60° C. and 500° C. For surgical drape applications where patient comfort is a factor, preferably at least 10 percent of the nonwoven fibers have lengths greater than about 0.06 cm (0.25 in.).

Preferred nonwoven fabric sheets include a layer of polyethylene film sandwiched between two layers of nonwoven rayon (commercially available as "Steri-Drape ® Blue Fabric" from 3M Company, Saint Paul, Minn.); melt-blown polypropylene fabric; and a combination of wood pulp and polyester fibers (commercially available as "Assure ® I, II, or III Nonwoven Fabric" from Dexter Corporation, Windsor Locks, Conn.).

Preferred woven or knit fabric sheets include muslin, cotton and silk.

Particularly-preferred nonwoven fabric sheets are made from spun-bonding or spun-lacing thermoplastic polymeric fibers. Particularly-preferred sheets include those made from spun-bonding thermoplastic polymeric fibers, wherein 100 percent of the fibers are melt-blown polypropylene fibers; spun-lacing thermoplastic polymeric fibers, wherein 100 percent of the fibers are polyester (commercially available as "Nexus ® 100% Polyester" from Burlington Formed Fabrics, Greensboro, N.C.); spun-bonding thermoplastic polymeric fibers, wherein 100 percent of the fibers are nylon fibers, (commercially available as "Cerex ® Spunbonded NYLON" from James River Corp., Simsonville, N.C.); and spun-bonding thermoplatic polymeric fibers, wherein 100 percent of the fibers are polyester (commercially available as "Reemay ® Spunbonded Polyester" from E. I. DuPont de Nemours and Co., Wilmington, Del.). While the particularly-preferred fabric sheets consist almost essentially of 100 percent by weight thermoplastic polymeric fibers, minor quantities of non-thermoplastic dyes and/or pigments may be present without destroying the particularly-preferred nature of the fabric.

Fabric sheets made of thermoplastic polymeric fibers are particularly preferred since they have a reduced tendency to flame when struck with a laser beam typically used in surgery. As illustrated by Examples 32–34, fabrics made from thermoplastic fibers resist flaming when subjected to 0.5 second strikes of a $CO_2$ laser beam, employing powers from 10–40 watts and beam widths from 0.6 to 5.8 mm. Flaming of the drape is an obvious hazard to the patient, particularly where sufficient oxygen and fuel (i.e., the drape itself) are present.

The thickness of fabric sheet 12 is determined by the intended use of the laser shield. Preferably for surgical drapes or gowns, fabric sheet 12 is about 0.01 to 3.00 mm thick and more preferably about 0.1 to 0.5 mm thick, to ensure good drapeability.

Metal layer 14 is preferably composed of metals or alloys which are ductile, highly reflective of a wide range of wavelengths of incident radiation, nontoxic and have high melting points. Preferred metal layers have rigidity values of less than about 60,000 kg.mm, preferably less than about 7,500 kg.mm and most preferably less than about 0.1 kg.mm. Also, preferred metal layers reflect at least 50 percent, and more preferably at least 95 percent of incident-laser radiation. Furthermore, preferred metals have melting temperatures of at least about 100° C.

Preferably metal layer 14 is a metal foil of aluminum, cerium, cobalt, copper, gold, indium, iron, lead, molybdenum, neodymium, nickel, palladium, platinum, praseiodymium, rhenium, rhodium, samarium, silver, tantalum, tin, titanium, tungsten, vanadium, zinc, and their alloys such as stainless steel. More preferred metal foils include aluminum, copper, gold, indium, nickel, niomium, palladium, platinum, rhenium, silver, titanium, stainless steel, and their alloys. Particularly-preferred metal foils include aluminum, nickel, gold, silver and stainless steel.

For surgical drape or gown applications the thickness of metal layer 14 should be sufficient to resist puncture by laser beams for a reasonable period of time. For example, the metal layer should be capaple of resisting puncture by a carbon dioxide laser beam having a 2.0 mm diameter focus and 5 watts of power for at least 0.2 second. Preferably, the metal layer is capable of resisting puncture by a carbon dioxide laser beam having a 0.4 mm diameter focus and 20 watts of power for at least one second, and more preferably at least five seconds. However, the metal layer should also be thin enough to provide flexibility to the drape. The metal layer should be thin enough to provide the entire drape with a rigidity of less than about 60,000 kg.mm, preferably less than about 7,500 kg.mm, and most preferably less than about 0.1 kg.mm. Preferably, the metal layer 14 has a thickness between about $2.5 \times 10^{-3}$ mm and 2.0 mm. More preferably the thickness of the metal layer is between about $3.0 \times 10^{-3}$ mm and 1.0 mm, and most preferably between about $6.0 \times 10^{-3}$ mm and 0.15 mm.

Bonding of metal layer 14 to the fabric sheet 12 is accomplished by adhesive layer 16, or by other suitable means, including mechanical fastening means such as sewing. Suitable adhesives for use as adhesive layer 16 include rubber adhesives; latex adhesives such as natural or synthetic rubbers, polyurethanes, acrylics, polyesters, polyamides, polyethers, and epoxides; hot-melt adhesives such as ethylene vinyl acetate, polyesters and polyamides; solvent-borne adhesives such as rubbers, polyurethanes, acrylics, polyesters, polyamides, polyesters and epoxies; starch derivatives such as dextrin and natural polymers; protein derivatives such as casein-based adhesives and animal glues; and silicone adhesives. Preferred adhesives include a styrene-butadiene rubber adhesive commercially available as "3M Super 77 Spray Adhesive" from 3M Co., St. Paul, Minn.; and an isooctylacrylate acrylic acid copolymer commercially available as "Medical Transfer Adhesive #1524" from 3M Co. Preferably, in order to maintain drapeability for surgical applications, adhesive layer 16 is no more than about 2 mm thick. Alternatively, where the fabric sheet is made from nonwoven polymeric fibers, the fabric sheet can be heat laminated to the metal layer eliminating the need for a separate adhesive layer 16.

For surgical applications, the laser shield illustrated in FIG. 1 is positioned so that metal layer 14 is closest to the patient and fabric sheet 12 is towards the laser. In this manner reflective glare is reduced. Additionally, aberrant strikes of the laser are easily detected since the laser immediately penetrates the top fabric sheet 12 revealing the metal foil below.

Figure 2:
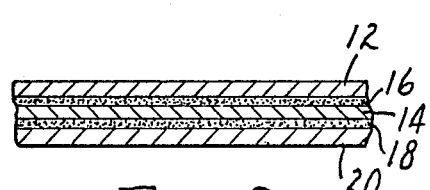
FIG. 2 is a cross-sectional view of a preferred embodiment of the invention.

A preferred embodiment of the present invention for surgical use is illustrated in FIG. 2 and includes a second fabric sheet 20 laminated to the underside of metal layer 14 by second adhesive layer 18. When in use second fabric sheet 20 is placed in contact with the skin of the patient resulting in a more comfortable drape when drapes which have metal layer 14 in contact with the patient.

It is particularly preferred that second fabric sheet 20 be made, at least on its exterior surface, of non-thermoplastic fibers, such as wood pulp and rayon or other non-thermoplastic materials such as woven or knit muslin, cotton or silk. Such non-thermoplastic materials do not melt when the surgical drape is struck by a laser beam, and act as an insulating layer protecting the tissue of the patient from the heat caused by the laser strike. A particularly preferred fabric sheet 20 is 3M's "Steri-Drape ® Blue Fabric."

Figure 3:
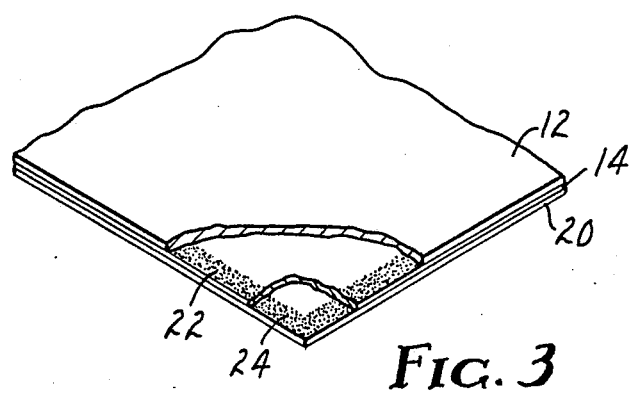
FIG. 3 is a perspective view of another construction of the laser shield of FIG. 2, some parts thereof broken away.

As shown in FIG. 2, metal layer 14 and fabric sheets 12 and 20 may be laminated together over their entire juxtaposed surfaces by adhesive layers 16 and 18, respectively. However, an alternative preferred embodiment, illustrated in FIG. 3, is to bond metal layer 14 to fabric sheets 12 and 20 with adhesive layers 22 and 24, respectively, disposed only along the periphery of the construction.

Figure 6:
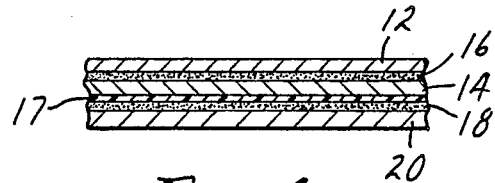
FIG. 6 is a cross-sectional view of another preferred embodiment of the invention.

Another preferred embodiment of the present invention, for use as a surgical drape, is illustrated in FIG. 6 and includes a polymeric film layer 17 disposed between metal layer 14 and second fabric sheet 20. Such an intermediate layer of polymeric film 17 has been found useful to protect the thin metal layer 14 from damage during handling. Suitable polymeric films include polyester, polypropylene, and polyethylene. Preferably polymeric film layer 17 has a thickness of between 0.006 and 0.15 mm. Thicker films would tend to interfere with the flexibility of the drape. Metal foil/polymeric film laminates can be used to provide metal layer 14 and film layer 17, respectively. Particularly-preferred metal foil/film laminates include a 0.018 mm thick, aluminum foil having a 0.013 mm thick polypropylene or polyester film extruded thereon, both available from Lamart, Corp., Clifton, N.J.

The constructions of the present invention may include a pressure-sensitive adhesive on portions of the patient side of the drape to aid in positioning the drape on the patient and keeping it out of the way of the surgeon. Referring to FIG. 2, the pressure-sensitive adhesive may be applied to second fabric sheet 20, or may be applied directly to metal layer 14 in place of second fabric sheet 20. Preferred pressure-sensitive adhesives include silicone-based adhesives and acrylate-based adhesive. A particularly-preferred pressure-sensitive adhesive is an isooctylacrylate acrylic acid copolymer commercially available as "Medical Transfer Adhesive No. 1524" from 3M Co.

Laser-resistant surgical drapes of this invention could also include other conventional accessories needed for the specific drape design, such as instrument pouches, fluid control pouches, and apertures.

For surgical applications, the laser barrier is cut to the desired shape, adhesive is applied to the patient side as needed and the drape is sterilized after packaging. The laser-resistant drape may be safely used (either wet or dry) in areas where laser energy is being applied to a patient so as to shield the patient from unintended laser radiation such as might occur by the accidental movement of the laser source or the patient.

Figure 4:
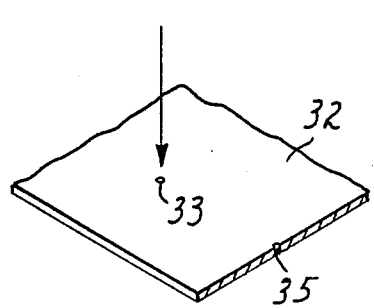
FIG. 4 is a prospective view of a portion of a conventional surgical drape, part thereof shown in section, with a laser beam puncturing the drape.
Figure 5:
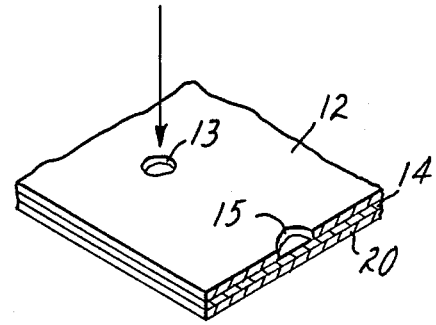
FIG. 5 is a perpective view of the construction of FIG. 2, part thereof shown in section, with a laser beam penetrating the top layer of the laser shield.

FIGS. 4 and 5 illustrate the unexpected ability of the laser shields of this invention to detect aberrant laser strikes. FIG. 4 illustrates a conventional surgical drape consisting of a sheet of nonwoven fabric material 32. The arrow represents a beam of laser radiation which strikes fabric sheet 32 and creates hole 33 therethrough. Hole 35 is a similarly-created hole shown in cross section. FIG. 5 illustrates a laser-resistant drape of this invention having fabric sheets 12 and 20 laminated to metal layer 14. The arrow in this figure represents a beam of laser radition (of the same intensity as that shown in FIG. 4) which strikes the drape and penetrates fabric sheet 12 producing hole 13 (shown slightly enlarged). Since metal layer 14 is not punctured by the laser beam, hole 13 reveals metal layer 14. Hole 15 (shown slightly enlarged) is a similarly-created hole shown in cross section. While an incident laser beam creates a hole of approximately the same area as the incident beam entirely through the conventional drape material of FIG. 4, the same laser beam will create a hole having an area at least twice that of the incident laser beam through only the top fabric sheet 12 of the laser barrier of this invention, revealing the shiny metal layer 14 underneath. Preferably the hole created through fabric sheet 13 will be from about two or ten times larger than the incident laser beam. Thus, while it is very difficult to detect where aberrant laser beams have struck conventional surgical drapes and possibly damaged the patient underneath, surgical drapes of this invention protect the patient against aberrant laser strikes and provide a large shiny mark indicating aberrant laser strikes. The surgeon upon observing the shiny mark can adjust the laser beam to prevent further aberrant laser beams from striking the drape and/or the patient.

For example, a 0.4 mm diameter laser beam from a $CO_2$ laser, having 20 watts of power, used at a 90° angle of incidence for pulses of 0.5 to 3.0 seconds creates a hole of approximately 0.2 to 0.3 mm² in conventional drape materials such as "Steri-Drape® Blue Fabric," and "Assure® I Nonwoven Fabric." The same beam does not puncture the laser-resistant drapes of this invention, but produces an easily-seen silver spot of approximately 0.3-0.6 mm² in area.

The laser shields of this invention are able to resist puncture by all commonly-used $CO_2$, Argon and Neodymium YAG laser for at least two seconds, and generally for greater than five seconds. Additionally, the laser shields are less flammable than the commonly-used cloth surgical drapes. For example, "Steri-Drape® Blue Fabric" surgical drape and "Assure® I Nonwoven Fabric" when tested using National Fire Protection Association Standard Test Method (NFPA STM) 702-1980 ignite in less than approximately 15 seconds. The laser-resistant surgical drapes of this invention when tested in accordance with the same procedure withstand ignition for at least about 20 seconds, and many of the drapes, particularly those having fabric sheet 12 made from thermoplastic fibers, do not ignite at all.

For surgical applications, the choice of whether to use a drape having the fabric sheets and metal layer laminated together over their entire juxtaposed surfaces, illustrated in FIG. 2, or a drape having the fabric sheets and metal layer bonded together only at their peripheries, illustrated in FIG. 3, will depend on the surgeon's determination of which properties of the drape are most important. As illustrated in Example 20, resistance to laser penetration is generally greater for the drape illustrated in FIG. 3. However, as shown in Example 21, the drape illustrated in FIG. 2 generally reflects less of the incident laser beam than the drape illustrated in FIG. 3. Thus, the drape illustrated in FIG. 2 will provide less reflective glare. Furthermore, the drape illustrated in FIG. 2 is generally less flammable than the drape illustrated in FIG. 3.

The following examples illustrate the construction, laser resistance, laser detection property, reflectivity and flammability of the laser shields of this invention.

EXAMPLE 1

A 30.5 cm by 30.5 cm square of nonwoven surgical drape material made from wood pulp and polyester fibers and having a thickness of about 0.16 mm, commercially available as "Assure® I Nonwoven Fabric" from Dexter Corporation, Windsor Locks, Conn., was sprayed with a styrene-butadiene rubber adhesive commercially available as "3M Super 77 Spray Adhesive" from 3M Co., St. Paul, Minn. After a wait of about 15 seconds, a 30.5 cm by 30.5 cm square of 0.015 mm thick aluminum foil was placed over the adhesive surface of the drape material and bonded thereto. A second 30.5 cm by 30.5 cm square of "Assure® I Nonwoven Fabric" was sprayed with "3M Super 77 Spray Adhesive" and laminated to the exposed aluminum foil side of the composite. The resulting laser-resistant drape consisted of aluminum foil laminated by adhesive layers between two layers of "Assure® I Nonwoven Fabric".

EXAMPLE 2

A laser-resistant drape was constructed in accordance with Example 1 except that instead of using "3M Super 77 Spray Adhesive," an isooctylacrylate acrylic acid copolymer commercially available as "Medical Transfer Adhesive No. 1524" from 3M Co. was used to laminate the two layers of "Assure® I Nonwoven Fabric" to the aluminum foil.

EXAMPLE 3

A laser-resistant drape was constructed in accordance with Example 2 execpt that the adhesive bonding the layers of fabric material and aluminum foil together was applied only along the periphery of the composite in a strip about 10.0 mm wide.

EXAMPLE 4

A laser-resistant drape was constructed in accordance with Example 1, except that instead of using "Assure® I Nonwoven Fabric" as the fabric sheets, a layer of polyethylene sandwiched between two layers of nonwoven rayon, having a thickness of 0.18 mm and commercially available as "Steri-Drape® Blue Fabric" from 3M Company, St. Paul, Minn. was employed.

EXAMPLE 5

This example illustrates the laser resistance of the drapes of Examples 1-4 and the ability of the drapes to detect where the laser has struck.

The laser-resistant drapes made in accordance with Examples 1-4 were compared with samples of "Assure® I Nonwoven Fabric," "Steri-Drape® Blue Fabric" and a 0.015 mm thick aluminum foil. Seconds required for the laser to puncture the sample and the appearance of the sample on the side facing the laser are reported in Table I below. The laser beam was 0.4 mm in diameter and was produced by a $CO_2$ laser having 20 watts of power. The laser struck the samples at a 90° C. angle. Laser exposure time was 5 seconds. The diameter of the holes in the fabric sheets was measured by the human eye using a micrometer.

TABLE I

| Material | Time to Puncture (seconds) | Appearance on Side Towards Laser |
|---|---|---|
| Aluminum foil | >5.0 | No visible effect |
| "Assure ® I Nonwoven Fabric" | <0.1 | ~0.4 mm diameter hole in fabric sheet |
| "Steri-Drape ® Blue Fabric" | <0.1 | ~0.4 mm diameter hole in fabric sheet |
| Example 1 | >5.0 | ~1.0 mm diameter hole in fabric sheet exposed aluminum foil |
| Example 2 | >5.0 | ~1.0 mm diameter hole in fabric sheet exposed aluminum foil |
| Example 3 | >5.0 | — |
| Example 4 | >5.0 | ~1.0 mm diameter hole in fabric sheet exposed aluminum foil |

None of the drapes of this invention were puncture by the laser. A hole was created in the fabric sheet and the aluminum foil underlying the fabric was exposed. The 0.4 mm holes through the "Assure® I Nonwoven Fabric" and "Steri-Drape® Blue Fabric" were very difficult to see unless the material had a bright light behind it. The hole through the fabric sheet of the drapes of Examples 1-4 was very easy to see since it was more than twice as large as the holes through the fabric material alone, and revealed the aluminum foil below. Thus, this example illustrates that the laser-resistant surgical drapes of this invention provide protection from lasers and easy detection of aberrant laser strikes.

EXAMPLE 6

A laser-resistant drape was constructed in accordance with Example 4 except that instead of having "Steri-Drape ® Blue Fabric" on both sides of the aluminum foil, it was only laminated to one side of the aluminum foil and a pressure-sensitive adhesive comprising an isooctylacrylate acrylic acid copolymer, commercially available as "Medical Transfer Adhesive No. 1524" from 3M Co., was applied to the other side of the aluminum foil.

EXAMPLE 7

A laser-resistant drape was constructed in accordance with Example 4 except that instead of having "Steri-Drape ® Blue Fabric" on both sides of the aluminum foil, it was only applied to one side of the aluminum foil and a 0.28 mm thick layer of polypropylene microfibers was applied to the other side using "3M Super 77 Spray Adhesive".

EXAMPLE 8

A laser-resistant drape was constructed in accordance with Example 1 except that instead of using "Assure ® I Nonwoven Fabric," the aluminum foil was sandwiched between 0.28 mm thick layers of polypropylene microfibers.

EXAMPLE 9

The surgical drapes made according to Examples 4 and 6 through 8 were placed on a metal table and struck at a 90° angle with a hand-held $CO_2$ laser using 20 watts and a 0.2 mm spot diameter. The length of the laser pulse varied from 0.5 to 5.0 sec. Effects on both sides of the drape were noted (towards and away from the laser) and are reported in Table II below. None of the composites were punctured in less than 2 seconds and many were not punctured after 5 seconds. The laser created a hole in the fabric layers of the drape, revealing the aluminum foil below. The diameter of the holes created in the fabric sheets was measured by the human eye using a micrometer.

TABLE II

| Material | Seconds of Pulse | Effects Toward the Laser | Effects Away from the Laser |
| --- | --- | --- | --- |
| Ex. 4 | 0.5 | 1 mm diameter hole exposed aluminum foil with some blackening around the edges | none |
| | 1.0 | 1 mm diameter hole exposed aluminum foil with some blackening around the edges | none |
| | 2.0 | 2 mm diameter hole exposed aluminum foil with some blackening around the edges | none |
| | 2.5 | 2 mm diameter hole exposed aluminum foil with some blackening around the edges | none |
| | 5.0 | 2 mm diameter hole exposed aluminum foil with some blackening around the edges | none |
| Ex. 6 ("Steri-Drape ® Blue Fabric" on laser side pressure-sensitive adhesive on table side) | 0.5 | 1 mm diameter hole exposed aluminum foil with some blackening around the edges | none |
| | 1.0 | 2 mm diameter hole exposed aluminum foil with some blackening around the edges | none |
| | 2.0 | 2 mm diameter hole exposed aluminum foil with some blackening around the edges | none |
| | 4.0 | 3 mm diameter hole exposed aluminum foil with some blackening around the edges | small puncture in aluminum foil |
| Ex. 7 ("Steri-Drape ® Blue Fabric" on laser side polypropylene on table side) | 0.5 | 1 mm diameter hole exposed aluminum foil with some blackening around the edges | 2 mm diameter hole exposed aluminum foil |
| | 1.0 | 1 mm diameter hole exposed aluminum foil with some blackening around the edges | 4 mm diameter hole exposed aluminum foil |
| | 2.0 | 3 mm diameter hole exposed aluminum foil with some blackening around the edges | 10 mm diameter hole exposed aluminum foil, with a small puncture in foil |
| | 3.5 | 2 mm diameter hole exposed aluminum foil with some blackening around the | 6 mm diameter hole exposed aluminum foil, |

TABLE II-continued

| Material | Seconds of Pulse | Effects Toward the Laser | Effects Away from the Laser |
| --- | --- | --- | --- |
| | | edges | very small puncture in foil |
| Ex. 7 | 0.5 | 1 mm diameter hole exposed aluminum foil | none |
| (polypropylene on laser side "Steri-Drape ® Blue Fabric" on table side) | 1.0 | 2 mm diameter hole exposed aluminum foil | none |
| | 2.0 | 3 mm diameter hole exposed aluminum foil | none |
| | 5.0 | 4 mm diameter hole exposed aluminum foil | none |
| Ex. 8 | 0.5 | 1 mm diameter hole exposed aluminum foil | 0.5 mm diameter hole exposed foil |
| | 1.0 | 2 mm diameter hole exposed aluminum foil | 0.5 mm diameter hole exposed foil |
| | 2.0 | 3 mm diameter hole exposed aluminum foil | 1 mm diameter hole exposed foil |
| | 5.0 | 3 mm diameter hole exposed aluminum foil | 1 mm diameter hole exposed foil |

EXAMPLE 10

A laser-resistant surgical drape according to this invention was constructed was follows. A 30.5 cm by 30.5 cm square of "Steri-Drape ® Blue Fabric" was laminated to a 0.015 mm thick 30.5 cm by 30.5 cm square of aluminum foil using 3M's "Medical Transfer Adhesive No. 1524".

EXAMPLE 11

A laser-resistant drape was constructed in accordance with Example 10 except that instead of using "Steri-Drape ® Blue Fabric," a fabric made of a layer of melt-blown polypropylene fibers between two layers of spunbonded polypropylene fibers, having a weight of 48.4 g/m$^2$ and a thickness of 0.23 mm, was used.

EXAMPLE 12

A laser-resistant drape was constructed in accordance with Example 10 except that instead of using "Steri-Drape ® Blue Fabric," "Assure ® I Nonwoven Fabric" was used.

EXAMPLE 13

A laser-resistant drape was constructed in accordance with Example 10 except that instead of using 3M's "Medical Transfer Adhesive No. 1524" as the adhesive, "3M Super 77 Spray Adhesive" was used.

EXAMPLE 14

A laser-resistant drape was constructed in accordance with Example 11 except that instead of using 3M's "Medical Transfer Adhesive No. 1524" as the adhesive, "3M Super 77 Spray Adhesive" was used.

EXAMPLE 15

A laser-resistant drape was constructed in accordance with Example 12 except that instead of using 3M's "Medical Transfer Adhesive No. 1524" as the adhesive, "3M Super 77 Spray Adhesive" was used.

EXAMPLE 16

The drapes made according to Examples 10–15 as well as 0.015 mm thick aluminum foil and conventional nonwoven surgical drape materials were placed on a metal table and tested with a $CO_2$ laser at 20 watts power using a 0.4 mm diameter beam and an incidence angle of 90°. The results are recorded in Table III below. The aluminum foil and the laser barriers of Examples 10–15 were not punctured even after 3.0 seconds of exposure, while the conventional drape materials were punctured after 0.5 second exposures. The diameter of the holes in the fabric layers was measured by the human eye using a micrometer.

TABLE III

| Material | Seconds of Pulse | Appearance on Side Towards Laser |
| --- | --- | --- |
| Aluminum Foil | 0.5 | No change |
| | 1.0 | No change |
| | 2.0 | No change |
| | 3.0 | No change |
| "Steri-Drape ® Blue Fabric" | 0.5 | 0.4 mm diameter hole |
| | 1.0 | 0.4 mm diameter hole |
| | 2.0 | 0.4 mm diameter hole |
| | 3.0 | 0.4 mm diameter hole |
| Spun-bonded polypropylene fibers[1] | 0.5 | 0.4 mm diameter hole |
| | 1.0 | 0.4 mm diameter hole |
| | 2.0 | 0.4 mm diameter hole |
| | 3.0 | 0.4 mm diameter hole |
| "Assure ® I, Nonwoven Fabric" | 0.5 | 0.4 mm diameter hole |
| | 1.0 | 0.4 mm diameter hole |
| | 2.0 | 0.4 mm diameter hole |
| | 3.0 | 0.4 mm diameter hole |
| Example 10 ("Steri-Drape ® Blue Fabric" on laser side) | 0.5 | 0.8 mm diameter hole exposed foil |
| | 1.0 | 0.8 mm diameter hole exposed foil |
| | 2.0 | 0.8 mm diameter hole exposed foil |
| | 3.0 | 0.8 mm diameter hole exposed foil |
| Example 11 (Spun-bonded polypropylene fibers on laser side) | 0.5 | 1.0 mm diameter hole exposed foil |
| | 1.0 | 1.0 mm diameter hole exposed foil |
| | 2.0 | 1.0 mm diameter hole exposed foil |
| | 3.0 | 1.0 mm diameter hole exposed foil |
| Example 12 ("Assure ® I Nonwoven Fabric" on laser side) | 0.5 | 0.7 mm diameter hole exposed foil |
| | 1.0 | 0.7 mm diameter hole exposed foil |
| | 2.0 | 0.7 mm diameter hole exposed foil |
| | 3.0 | 0.7 mm diameter hole exposed foil |
| Example 13 ("Steri-Drape ® Blue Fabric" on laser side) | 0.5 | 0.8 mm diameter hole exposed foil |
| | 1.0 | 0.8 mm diameter hole exposed foil |
| | 2.0 | 0.8 mm diameter hole exposed foil |
| | 3.0 | 0.8 mm diameter hole exposed foil |
| Example 14 (Spun-bonded polypropylene fibers on laser side) | 0.5 | 1.0 mm diameter hole exposed foil |
| | 1.0 | 1.0 mm diameter hole exposed foil |
| | 2.0 | 1.0 mm diameter hole exposed foil |
| | 3.0 | 1.0 mm diameter hole exposed foil |
| Example 15 ("Assure ® I Nonwoven Fabric" on laser side) | 0.5 | 0.6 mm diameter hole exposed foil |
| | 1.0 | 0.6 mm diameter hole exposed foil |
| | 2.0 | 0.6 mm diameter hole exposed foil |
| | 3.0 | 0.6 mm diameter hole exposed foil |

[1]A layer of melt-blown polypropylene fibers between two layers of spun-bonded polypropylene fibers, having a weight of 48.4 g/m$^2$ and an average thickness of 0.23 mm.

The laser created a hole in the fabric layer of the drapes of this invention, revealing the aluminum foil layer below. Table III illustrates that the laser produced holes in the fabric sheets of the drapes of this invention are much larger (at least about twice as large) and easier to see (due to both their size and the exposed aluminum foil) than the holes produced in conventional drape materials. Accordingly, the drapes of this invention offer easy detection of aberrant laser strikes.

EXAMPLE 17

A laser-resistant drape was constructed in accordance with Example 10, except that the adhesive was applied only along the periphery of the composite in a strip about 10.0 mm wide.

EXAMPLE 18

A laser-resistant drape was constructed in accordance with Example 11, except that the adhesive was applied only along the periphery of the composite in a strip about 10.0 mm wide.

EXAMPLE 19

A laser-resistant drape was constructed in accordance with Example 12, except that the adhesive was applied only along the periphery of the composite in a strip about 10.0 mm wide.

EXAMPLE 20

Resistance to laser puncture for drapes having the fabric sheet and the metal layer laminated together over their entire juxtaposed surfaces (Examples 10-12) and those having the fabric sheet and metal layer adhered only along the periphery of the composite (Examples 17-19) was compared according to the following example.

The laser puncture resistance of the drapes of Examples 10-12 (laminated composites), the drapes of Examples 17-19 (bonded only at periphery), 0.015 mm thick aluminum foil, wet linen (each layer, when dry, 1.3 mm thick, weighing 363 g/M$^2$) and wet gauze (when dry, 0.67 mm thick, weighing of 292 g/M$^2$) was measured as follows. A $CO_2$ laser, using 20 watts of power with a 0.4 mm diameter focus was used to strike the samples at both a 45° and 90° angle. The samples were positioned so that the fabric sheet was closest to the laser. Laser exposure time was 5 seconds. Whether or not the sample was punctured by the laser and the time required for such puncture is reported in Table IV. "DNP" indicates that the laser beam did not puncture the sample.

TABLE IV

| | Time to puncture (seconds) | | | | | | | | | |
|---|---|---|---|---|---|---|---|---|---|---|
| | 45° incident beam Trials | | | | | 90° incident beam Trials | | | | |
| Material | #1 | #2 | #3 | #4 | #5 | #1 | #2 | #3 | #4 | #5 |
| Aluminum foil | DNP | DNP | DNP | DNP | DNP | DNP | DNP | DNP | DNP | DNP |
| Wet woven cotton (1 layer) | 0.5 | 0.5 | 0.5 | 0.5 | 0.5 | 0.5 | 0.5 | 0.5 | 0.5 | 0.5 |
| Wet woven cotton (2 layers) | DNP | DNP | DNP | 5.0 | DNP | 0.5 | 2.0 | 0.5 | 0.5 | 0.5 |
| Wet woven cotton (3 layers) | DNP | DNP | DNP | DNP | DNP | DNP | DNP | DNP | DNP | 2.0 |
| Wet woven cotton gauze | DNP | DNP | 3.0 | DNP | 3.0 | 1.5 | DNP | DNP | 4.0 | DNP |
| Example 10 | DNP | DNP | DNP | DNP | DNP | DNP | DNP | DNP | DNP | 2.0 |
| Example 11 | DNP | DNP | DNP | DNP | DNP | DNP | DNP | DNP | DNP | DNP |
| Example 12 | DNP | DNP | DNP | DNP | DNP | DNP | 5.0 | 5.0 | DNP | DNP |
| Example 17 | DNP | DNP | DNP | DNP | DNP | DNP | DNP | DNP | DNP | DNP |
| Example 18 | DNP | DNP | DNP | DNP | DNP | DNP | DNP | DNP | DNP | DNP |
| Example 19 | DNP | DNP | DNP | DNP | DNP | DNP | DNP | DNP | DNP | DNP |

Several of the drapes made according to Example 12 and one of the drapes made according to Example 10 were punctured by the 90° incident laser beam in 2.0-5.0 seconds while none of the drapes made according to Examples 17-19 were punctured by the laser beam. Thus, it appears that the drapes which have the fabric sheet and the metal layer bonded together only at their peripheries (Examples 17-19) provide better resistance to laser puncture than do the drapes which have the fabric sheet and metal layer laminated together over their entire juxtaposed surfaces (Examples 10-12).

EXAMPLE 21

This example illustrates the ability of the laser shields of this invention to reflect an incident laser beam. Reflectivity of shields having the fabric sheet and the metal layer laminated together over their entire juxtaposed surfaces (Examples 10-12) was compared with reflectivity of shields having the two layers bonded only at their peripheries (Examples 17-19).

The laser-resistant drapes of Examples 10-12 and 17-19, as well as 0.015 mm thick aluminum foil, were struck with a 0.4 mm laser beam produced by a $CO_2$ laser having 20 watts of power, at a 45° angle. A paper target was placed 25.4 cm from the sample and in the path of the reflected laser beam. The time required to char the target is recorded in Table V below.

TABLE V

| | Time Required to Char Target (Seconds) | | | | | |
|---|---|---|---|---|---|---|
| Material | #1 | #2 | #3 | #4 | #5 | Average |
| Aluminum foil | 0.5 | 0.5 | 0.5 | 0.5 | 0.5 | 0.5 |
| Example 10 | 5.0 | 2.5 | 5.0 | 2.0 | 1.0 | 3.1 |
| Example 11 | 2.5 | 2.5 | 4.0 | 2.0 | 2.5 | 2.7 |
| Example 12 | 1.5 | 1.0 | 4.5 | 2.5 | 2.5 | 2.4 |
| Example 17 | 0.5 | 1.5 | 0.5 | 0.5 | 0.5 | 0.7 |
| Example 18 | 0.5 | 1.5 | 0.5 | 0.5 | 0.5 | 0.7 |
| Example 19 | 4.0 | 0.5 | 1.5 | 0.5 | 0.5 | 1.4 |

The drapes of Examples 17-19 charred the target in a shorter period of time than the drapes of Examples 10-12, indicating that the drapes of Examples 17-19 reflect more of the incident laser radiation than the drapes of Examples 10-12. Thus, where reduced reflection is desired, drapes having the fabric sheet laminated to the metal layer over their entire juxtaposed surfaces (Examples 10-12) are preferred over drapes having the fabric and metal layers bonded together only at their peripheries (Examples 17–19).

EXAMPLE 22

A laser-resistant drape was constructed in accordance with Example 10 except that a sheet of woven cotton linen (0.67 mm thick, with a weight of 292 g/M$^2$, commercially available as "13 Count Linen" from Lintex Corp., Minneapolis, Minn.) was used instead of "Steri-Drape ® Blue Fabric" as the fabric sheet.

EXAMPLE 23

The example illustrates the flammability of the laser-resistant drapes of this invention. The drapes of Examples 10, 12, 17, 19 and 22 as well as woven cotton linen (Lintex's "13 Count Linen") and conventional surgical drape materials were tested in accordance with National Fire Protection Association Standard Test Method (NFPA STM) 702-1980, incorporated herein by reference. The samples (5.08 cm × 15.24 cm) were positioned at an incline and exposed at their bottom edges to a gas a flame for 10 seconds. The time required for ignition and propagation of the flame to the top of the sample, and the percent of the sample burned are recorded in Table VI below.

TABLE VI

| Material | Time for Ignition and Propagation to Top of Sample (seconds) | Percent of Sample Burned | Comments |
| --- | --- | --- | --- |
| Linen | 39.0 | 100% | Once sample ignited, very difficult to blow out flame |
| "Steri-Drape ® Blue Fabric" | 9.3 | 100% | Once sample ignited, propagation was very fast |
| "Assure ® I Nonwoven Fabric" | 13.0 | 100% | Once sample ignited, propagation was very fast |
| Example 22 | Does not ignite | | Slight brown spot |
| Example 10 | Does not ignite | | Slight discoloration of fabric sheet |
| Example 12 | Does not ignite | | Slight char |
| Example 17 | 32.6 | 100% | |
| Example 19 | 22.9 | 100% | |

This example illustrates that the fabric sheet and metal layer composites of this invention are more flame retardant than conventional fabric drapes. A comparison of the laser-resistant drapes having the fabric sheet and metal layer laminated together over their entire juxtaposed surfaces (Examples 10 and 12) with those having the two layers bonded together only along their periphery (Examples 17–19) illustrates that the laminated (Examples 10 and 12) composites are more flame retardant than those bonded together only along the periphery (Examples 17 and 19).

EXAMPLE 24

A laser-resistant drape was prepared in accordance with Example 10 except that 0.023 mm thick copper foil was used in place of aluminum foil. The drape was exposed to ten 5-second pulses from a CO$_2$ laser at a 90° angle of incidence. The laser beam was 0.4 mm in diameter and used 20 watts of power. The laser beam failed to puncture the drape.

EXAMPLE 25

The laser-resistant drapes of Examples 10, 12 and 24 were exposed to five 5-second pulses from an argon laser at a 90° angle of incidence. The laser beam was 0.13 mm in diameter and used 1.6 watts of power. None of the drapes were punctured by the laser.

EXAMPLE 26

A 30 cm by 30 cm square of fabric made of a layer of melt-blown polypropylene fibers between two layers of spun-bonded polypropylene fibers, having a weight of 48.4 g/m$^2$ and an average thickness of 0.23 mm, was laminated to one side of a 30 cm by 30 cm square of 0.18 mm thick aluminum foil (alloy #1145-0) using 3M's "Medical Transfer Adhesive No. 1524." The fabric and aluminum foil were laminated together over their entire juxtaposed surfaces. To the other side of the aluminum foil was laminated, in the same manner as above, a 30 cm by 30 cm sheet of "Steri-Drape ® Blue Fabric."

EXAMPLE 27

A drape was constructed in accordance with Example 26, except that instead of using fabric made of polypropylene fibers, fabric made of spun-laced fibers, 100 percent by weight of which are polyester, having a weight of 37.23 g/m$^2$ and available from Kendall Co., Boston, Mass. was used.

EXAMPLE 28

A drape was constructed in accordance with Example 26 except that the fabric made of polypropylene fibers was replaced with a fabric made of spun-bonded nylon fibers, having a weight of 67.69 g/m$^2$ and commercially available as "Cerex ® Spunbonded NYLON" from James River Corp., Neenah, Wis.

EXAMPLE 29

A drape was constructed in accordance with Example 26, except that the fabric made of polypropylene fibers was replaced with fabric made from a polypropylene fiber blend, commercially available as "Kimguard ® Sterilization Wrap" from Kimberly Clark Corp., Roswell, Ga.

EXAMPLE 30

A drape was constructed in accordance with Example 26, except that the fabric made of polypropylene fibers was replaced with a fabric made from 45 percent by weight polyester fibers and 55 percent by weight wood pulp, commercially available as "Sontara ® Spunlaced Fabric" from E. I. DuPont de Nemours and Co.

EXAMPLE 31

A drape was constructed in accordance with Example 26, except that the fabric made of polypropylene fibers was replaced with a fabric made from wood pulp and polyester fibers and treated with a flame retardant, commercially available as "Flame Retardant Apparel Fabric, N9372N" from The Dexter Corp., Windsor Locks, Conn.

EXAMPLE 32

The flame resistance of the drapes of Examples 26–28, which include a thermoplastic layer, was compared with the flame resistance of the drapes of Examples 4 and 29–31 according to the following procedure.

A $CO_2$ laser, commercially available from Sharplan ™ Lasers, Inc., Allendale, N.J., was mounted to a microscope, commercially avaliable as a "Zeiss Microscope OPM1" from Carl Zeiss, Inc., Thornwood, N.Y., using a microslad, commercially available as a "Sharplan ™ 719 Microslad" from Sharplan ™ Lasers, Inc. The "Sharplan ™ 719 Microslad" was fitted with a micromanipulator and a continuously variable defocus (CVD). The CVD allowed the laser beam to be broadened or narrowed over a certain range, enabling the testing of laser strikes of varying widths or spot sizes on the test drapes. The absolute power of the laser beam was varied to show the effect of a variety of laser powers and energy densities. The drape samples were placed 300 mm away from the laser and positioned so that the laser struck the samples at a 90° angle. The "Steri-Drape ® Blue Fabric" layer of each drape was placed laser side down. The laser exposure time for each strike was 0.5 second. The appearance of flames on each drape after being struck with the laser at powers between 20 and 40 watts and beam widths between 1.1 and 5.1 mm is reported in Table VII. Numbers 0 through 5 are used to represent the following:

0 = smoke, no other visible effects
1 = very small flash of light, no visible flame
2 = barely visible flame
3 = less than 1.3 cm flame extending from the fabric
4 = 1.3 to 2.5 cm flame extending from the fabric
5 = greater than 2.5 cm flame extending from the fabric Each test was repeated three times. The number reported in Table VII is the result of adding the numbers obtained after each strike.

the intensity (watts per unit cross section) decreases as the beam width increases.

The drape of Example 26, which had a thermoplastic polypropylene fabric closest to the laser resisted flame production at all beam widths and powers. The drape of Example 27, which had a thermoplastic polyester fabric closest to the laser resisted flame production, except for minor flame effects at the highest (40 watt) power setting. Similarly, the drape of Example 28, which had a thermoplastic nylon fabric closest the laser resisted flame production at all but the highest power setting. The reasons for the occassional flames noted in the drapes utilizing a thermoplastic fabric (Examples 26–28) are not understood, but may be connected with factors such as fabric density, fiber orientation, residual monomer in the polymer, etc.

EXAMPLE 33

A drape was constructed in accordance with Example 26, expect that the aluminum foil was replaced with a laminate of 0.018 mm thick aluminum foil (alloy #1145-0) and 0.013 mm thick polypropylene film, available from Lamart Corp., Clifton, N.J., and the fabric made from polypropylene fibers was replaced with a fabric made of polyester fibers and having a weight of 44 g/m², commercially available as "Nexus ® 100% Polyester" from Burlington Formed Fabrics, Greenboro, N.C. When this drape was tested for flame resistance in accordance with Example 32, the cumulative score for all three laser strikes was zero, at all beam widths and powers.

EXAMPLE 34

TABLE VII

| | | 10 Watts Beam Width (mm) | | | | | 20 Watts Beam Width (mm) | | | | | 30 Watts Beam Width (mm) | | | | | 40 Watts Beam Width (mm) | | | | |
|---|---|---|---|---|---|---|---|---|---|---|---|---|---|---|---|---|---|---|---|---|---|
| Ex. | Description of Fabric Layer | 1.1 | 2.1 | 3.1 | 4.1 | 5.1 | 1.1 | 2.1 | 3.1 | 4.1 | 5.1 | 1.1 | 2.1 | 3.1 | 4.1 | 5.1 | 1.1 | 2.1 | 3.1 | 4.1 | 5.1 |
| 26 | Spun-bonded fibers (100% polypropylene) | 0 | 0 | 0 | 0 | 0 | 0 | 0 | 0 | 0 | 0 | 0 | 0 | 0 | 0 | 0 | 0 | 0 | 0 | 0 | 0 |
| 27 | Spun-laced fibers (100% polyester) | 0 | 0 | 0 | 0 | 0 | 0 | 0 | 0 | 0 | 0 | 0 | 0 | 0 | 0 | 0 | 0 | 0 | 5 | 0 | 0 |
| 28 | Spun-bonded nylon fibers | 0 | 0 | 0 | 0 | 0 | 0 | 0 | 0 | 0 | 0 | 0 | 0 | 0 | 0 | 0 | 0 | 0 | 8 | 0 | 0 |
| 4 | Layer of polyethylene film between two layers nonwoven rayon | 0 | 0 | 0 | 0 | 0 | 0 | 0 | 15 | 15 | 0 | 0 | 0 | 15 | 15 | 12 | 0 | 0 | 15 | 15 | 15 |
| 29 | Polypropylene fiber blend | 0 | 0 | 0 | 0 | 0 | 0 | 0 | 0 | 0 | 0 | 0 | 3 | 12 | 15 | 15 | 0 | 0 | 12 | 9 | 0 |
| 30 | 45% by wt. polyethylene fibers 55% by wt. wood pulp | 0 | 3 | 12 | 10 | 0 | 0 | 0 | 15 | 15 | 0 | 0 | 0 | 15 | 15 | 15 | 0 | 0 | 15 | 15 | 0 |
| 31 | Wood pulp and polyester fibers treated with a flame retardant | 0 | 0 | 0 | 0 | 0 | 0 | 12 | 12 | 12 | 12 | 15 | 15 | 15 | 15 | 15 | 15 | 15 | 15 | 15 | 15 |

As seen from Table VII, when a beam width of about 1.1 mm was used (frequently the case in laser surgery) all of the drapes resisted flame production at beam powers in excess of 20 watts. As the power was raised, the drapes of Examples 4 and 29–31, which do not have a thermoplastic fabric layer closest to the laser, began to fail. As the beam width was increased, the failures increased, with an apparent maximum between beam widths of 3 and 4 mm. This result was unexpected since A drape was constructed in accordance with Example 26, except that the aluminum foil was replaced with a laminate of 0.018 mm thick, aluminum foil (alloy #1145-0) and 0.013 mm thick polyester film, available from Lamart Corp., and the fabric made from polypropylene fibers was replaced with a fabric made of polyester fibers and having a weight of 492 g/m² available from Kendall Co., Boston, Mass. When this drape was tested for flame resistance in accordance with Example 32, the cumulative score for all three strikes was zero at all beam widths and powers.

What is claimed is:

1. A laser-resistant surgical drape comprising an opaque, flexible, fabric sheet having one major surface juxtaposed with a reflective surface of a metal foil, said fabric sheet having about 40 or less pieces of lint/cm$^2$; said metal foil having a thickness sufficient to resist puncture by a CO$^2$ laser beam, 0.4 mm in diameter, using 20 watts of power for at least one second; and said fabric sheet and said metal foil having thicknesses sufficient to provide said laser-resistant surgical drape with a rigidity of less than about 0.1 kg·mm.

2. A laser shield for use in the field of operation during laser surgery comprising an opaque, flexible fabric sheet having one major surface juxtaposed with a reflective surface of a metal foil, said fabric sheet comprising nonwoven, knit or woven material, and said fabric sheet having about 40 or less pieces of lint/cm$^2$; and said metal foil having a thickness sufficient to
    (a) resist puncture by a CO$^2$ laser beam, 0.4 mm in diameter, using 20 watts of power for at least one second, and
    (b) provide said laser shield with a rigidity of less than about 60,000 kg·mm.

3. A laser-resistant surgical drape consisting essentially of first and second opaque, flexible fabric sheets, said first fabric sheet having a major surface juxtaposed with a reflective surface of a metal foil and said second fabric sheet having a major surface juxtaposed with the opposite side of said metal foil, such that said metal foil is sandwiched between said first and second fabric sheets, and first and second adhesive layers disposed between said first and second fabric sheets; wherein said first fabric sheet comprises thermoplastic polymeric fibers and said second fabric sheet is comprised of non-thermoplastic materials, and wherein both said first and second fabric sheets have about 40 or less pieces of lint/cm$^2$; and wherein said metal foil has a thickness sufficient to resist puncture by a CO$^2$ laser beam, 0.4 mm in diameter, using 20 watts of power for at least one second; and said fabric sheets and said metal foil have thicknesses sufficient to provide said laser-resistant surgical drape with a rigidity of less than about 0.1 kg·mm.

4. A laser shield for use in the field of operation during laser surgery comprising an opaque, flexible fabric sheet having one major surface juxtaposed with a reflective surface of a metal foil, said fabric sheet having about 40 or less pieces of lint/cm$^2$; said metal foil haing a thickness sufficient to resist puncture by a CO$_2$ laser beam, 2.0 mm in diameter, using 5 watts of power for at least 0.2 second; and said fabric sheet and said metal foil having thicknesses sufficient to provide said laser shield with a rigidity of less than about 60,000 kg·mm.

5. The laser shield of claim 1 wherein said fabric sheet comprises nonwoven materials selected from the group consisting of wood pulp, thermoplastic polymeric fibers, cellulosic fibers and combinations thereof.

6. The laser shield of claim 1 wherein said fabric sheet comprises woven or knit muslin, silk or cotton.

7. The laser shield of claim 1 wherein said metal foil comprises metals selected from the group consisting of aluminum, cerium, cobalt, copper, gold, indium, iron, lead, molybdenum, neodymium, nickel, palladium, platinum, praseodymium, rhenium, rhodium, samarium, silver, tantalum, tin, titanium, tungsten, vanadium, zinc, and alloys thereof.

8. The laser shield of claim 1 wherein said fabric sheet is held in juxtaposition with said metal foil by use of adhesive means, mechanical fastening means or heat lamination.

9. A laser-resistant surgical drape comprising an opaque, flexible, fabric sheet having one major surface juxtaposed with a reflective surface of a metal foil, said fabric sheet having about 40 or less pieces of lint/cm$^2$; said metal foil having a thickness sufficient to resist puncture by a CO$_2$ laser beam, 2.0 mm in diameter, using 5 watts of power for at least 0.2 second; and said fabric sheet and said metal foil having thicknesses sufficient to provide said laser-resistant surgical drape with a rigidity of less than about 0.1 kg·mm.

10. The laser-resistant surgical drape of claim 9 wherein said fabric sheet comprises non-woven materials selected from the group consisting of wood pulp, thermoplastic polymeric fibers, cellulosic fibers and combinations thereof.

11. The laser-resistant surgical drape of claim 10 wherein said nonwoven material is a thermoplastic polymeric fiber selected from the group consisting of polypropylene, polyester, polyethylene, polyolefin, polyamide and nylon fibers.

12. The laser-resistant surgical drape of claim 9 wherein said fabric sheet comprises woven or knit muslin, silk or cotton.

13. The laser-resistant surgical drape of claim 9 wherein said metal foil comprises metals selected from the group consisting of aluminum, cerium, cobalt, copper, gold, indium, iron, lead, molybdenum, neodymium, nickel, palladium, platinum, praseodymium, rhenium, rhodium, samarium, silver, tantalum, tin, titanium, tungsten, vanadium, and zinc foils, and foils which are alloys thereof.

14. The laser-resistant surgical drape of claim 9 wherein said fabric sheet has a thickness of between about 0.01 and 3.0 mm and said metal foil has a thickness of between about $2.5 \times 10^{-3}$ and 2.0 mm.

15. The laser-resistant surgical drape of claim 9 wherein said fabric sheet is held in juxtaposition with said metal foil by use of adhesive means, mechanical fastening means or heat lamination.

16. The laser-resistant surgical drape of claim 9 wherein said drape further comprises at least one adhesive foil disposed between said fabric sheet and said metal foil, said adhesive holding said fabric sheet in juxtaposition with said metal layer.

17. The laser-resistant surgical drape of claim 16 wherein said adhesive is selected from the group consisting of rubber adhesives, latex adhesives, hot-melt adhesives, solvent-borne adhesives, starch derivative adhesives, protein derivative adhesives and silicone adhesives.

18. The laser-resistant surgical drape of claim 9 wherein said drape further comprises a second fabric sheet having a major surface juxtaposed with said metal foil such that said metal foil is sandwiched between said fabric sheets, and first and second adhesive layers disposed between said fabric sheets and said metal foil, wherein said second fabric sheet has about 40 or less pieces of lint/cm$^2$.

19. The laser-resistant surgical drape of claim 18 wherein said first and second adhesive layers are disposed only along the periphery of said fabric sheets and metal foil.

20. The laser-resistant surgical drape of claim 18 wherein said second fabric sheet is comprised of non-thermoplastic materials, and said other fabric sheet comprises thermoplastic polymeric fibers.

21. The laser-resistant surgical drape or claim 20 wherein said non-thermoplastic material is selected from the group consisting of wood pulp, rayon, muslin, cotton and silk, said thermoplastic polymeric fibers are selected from the group consisting of polypropylene, polyester and nylon fibers, and said metal foil has a thickness of between about $6.0 \times 10^{-3}$ and 0.15 mm.

22. The laser-resistant surgical drape of claim 18 wherein said drape further comprises a thermoplastic polymeric film disposed between said metal foil and said second fabric sheet.

23. The laser-resistant surgical drape of claim 18 wherein said drape further comprises a pressure-sensitive adhesive applied to the major exterior surface of at least one fabric sheet.

24. A method of shielding operating room personnel, equipment and surgical patients from laser radiation in a field of surgery where lasers are being used comprising covering said personnel, equipment or patient with the laser shield of claim 1, said shield being positioned so that said fabric sheet is towards said laser.

25. A method of shielding patient from laser radiation during laser surgery comprising applying the laser-resistant surgical drape of claim 6 to the patient so as to shield the patient from unintended laser radiation, said drape positioned such that said fabric sheet is towards the laser and said metal foil is closest to the patient.

26. A method of shielding a patient from laser radiation during laser surgery comprising applying the laser-resistant surgical drape of claim 20 to the patient so as to shield the patient from unintended laser radiation, said drape positioned such that said second fabric sheet is closest to the patient.

* * * * *

UNITED STATES PATENT AND TRADEMARK OFFICE
CERTIFICATE OF CORRECTION

PATENT NO. : 4,901,738

DATED : February 20, 1990

INVENTOR(S) : Robert H. Brink, James H. C. Harper and Steven T. Link

It is certified that error appears in the above-identified patent and that said Letters Patent is hereby corrected as shown below:

The title on the front page should read --Laser Shield for Surgical Application--.

In Column 1, line 1, the title should read --Laser Shield for Surgical Application--.

In Column 3, line 12, ""Scotch"" should be --"Scotch$^R$--.

In the Claims
In Column 22, line 9, "6" should be --9--.

Signed and Sealed this

Second Day of April, 1991

Attest:

HARRY F. MANBECK, JR.

*Attesting Officer*  *Commissioner of Patents and Trademarks*